(12) United States Patent
Sullivan

(10) Patent No.: US 8,979,766 B2
(45) Date of Patent: Mar. 17, 2015

(54) SENSOR SYSTEM

(75) Inventor: Colin Edward Sullivan, Balmain (AU)

(73) Assignee: Sonomedical Pty. Ltd., Balmain, New South Wales (AU)

( * ) Notice: Subject to any disclaimer, the term of this patent is extended or adjusted under 35 U.S.C. 154(b) by 1127 days.

(21) Appl. No.: 12/663,599

(22) PCT Filed: Jun. 10, 2008

(86) PCT No.: PCT/AU2008/000825
§ 371 (c)(1),
(2), (4) Date: Jun. 8, 2010

(87) PCT Pub. No.: WO2008/148172
PCT Pub. Date: Dec. 11, 2008

(65) Prior Publication Data
US 2010/0256512 A1    Oct. 7, 2010

(30) Foreign Application Priority Data
Jun. 8, 2007    (AU) ................................ 2007903117

(51) Int. Cl.
*A61B 5/08* (2006.01)
*G01H 11/00* (2006.01)
*A61B 5/113* (2006.01)
(Continued)

(52) U.S. Cl.
CPC .............. *G01H 11/00* (2013.01); *A61B 5/113* (2013.01); *A61B 5/6887* (2013.01); *A61B 7/003* (2013.01); *A61G 2203/36* (2013.01)
USPC .......................................... 600/534; 600/529

(58) Field of Classification Search
CPC .... A61B 5/113; A61B 5/6892; A61B 5/6887; A61B 2562/0204; A61B 2562/0247

USPC .......................... 600/529–534, 500–504, 595
See application file for complete search history.

(56) References Cited

U.S. PATENT DOCUMENTS

| 5,479,932 A | 1/1996 | Higgins et al. |
| 5,989,193 A | 11/1999 | Sullivan |
| 6,491,647 B1 * | 12/2002 | Bridger et al. ................ 600/585 |

(Continued)

FOREIGN PATENT DOCUMENTS

| JP | S6092505 A | 5/1985 |
| WO | 0164103 A1 | 9/2001 |

(Continued)

*Primary Examiner* — Patricia Millari
*Assistant Examiner* — Tiffany Weston
(74) *Attorney, Agent, or Firm* — Browdy and Neimark, PLLC

(57) ABSTRACT

A sensor system comprises a mat (20) for placement over a patient's mattress including a number of sensors (10) located in the mat. The sensors include a sensor housing (12), a sound vibration sensing element in the form of a PVDF membrane (13), and means for amplifying sensed sounds. The PVDF membrane is coated/covered with a typically latex, impedance matching layer (14). The sensor automatically provides for auscultation, in which the patient's own weight, from the patient lying on the bed, compresses their thorax against the membrane, compressing also the patient's clothing, bed sheet and mattress cover material between the two. The recoil in the mattress opposes the body mass, thus compressing the membrane against the thorax. The impedance matching layer on top of the membrane transmits fine breath sounds through to the membrane as the latex does not weaken or attenuate the fine breath sounds but transmits them to the PVDF membrane. However being flexible, it is not uncomfortable to lie on.

17 Claims, 2 Drawing Sheets

(51) Int. Cl.
*A61B 5/00* (2006.01)
*A61B 7/00* (2006.01)

(56) References Cited

U.S. PATENT DOCUMENTS

| | | | |
|---|---|---|---|
| 6,547,743 | B2 | 4/2003 | Brydon |
| 6,988,993 | B2 | 1/2006 | Sullivan et al. |
| 2003/0163055 | A1* | 8/2003 | McLaughlin et al. ........ 600/504 |
| 2004/0111045 | A1 | 6/2004 | Sullivan et al. |
| 2008/0132808 | A1 | 6/2008 | Lokhorst |

FOREIGN PATENT DOCUMENTS

| | | | | |
|---|---|---|---|---|
| WO | WO 01/64103 | * | 9/2001 | ............... A61B 5/08 |
| WO | WO0197691 | A1 | 12/2001 | |
| WO | 2004006768 | A1 | 1/2004 | |
| WO | 2004045407 | A1 | 6/2004 | |

* cited by examiner

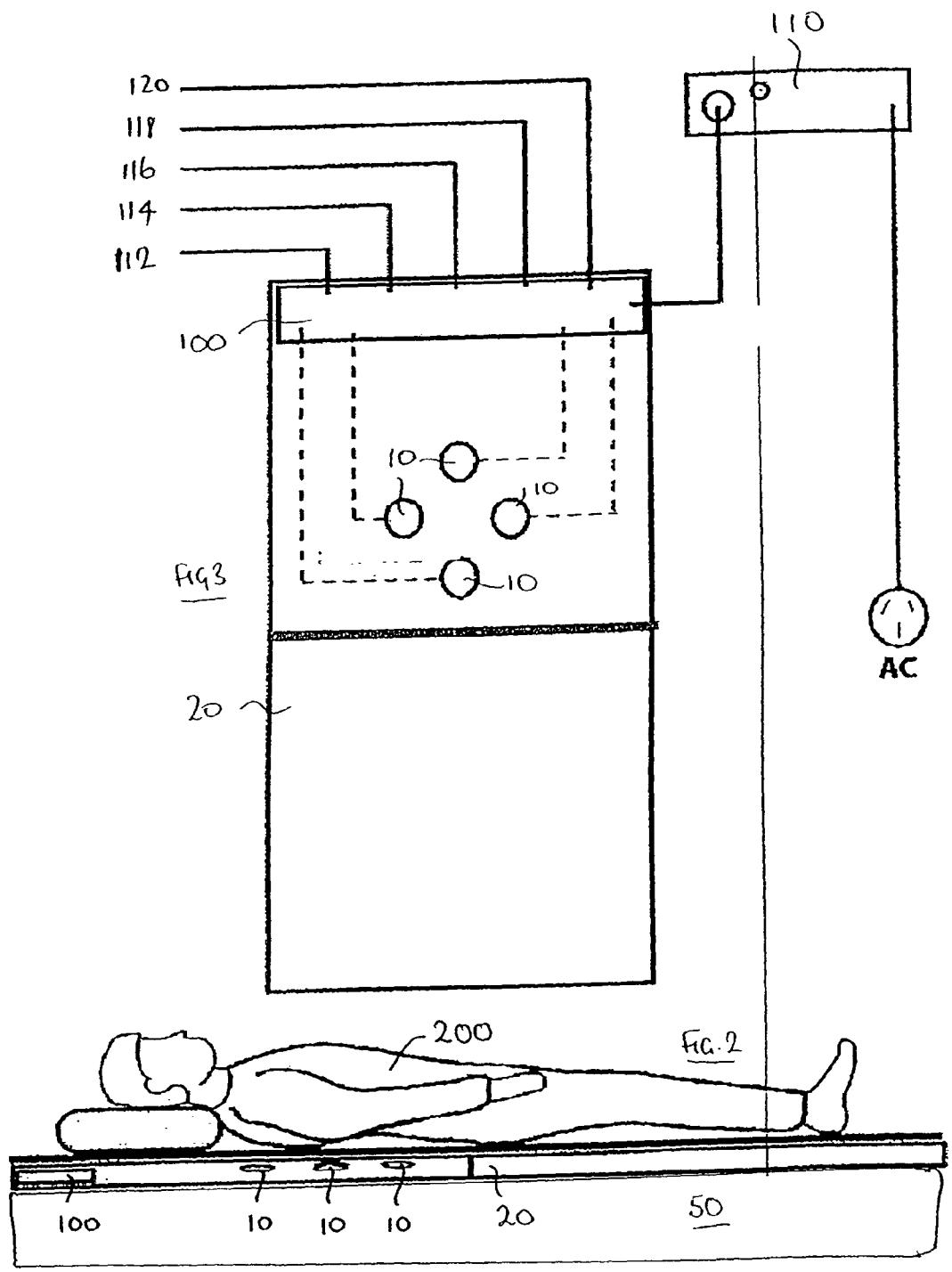

SENSOR SYSTEM

CROSS-REFERENCE TO RELATED APPLICATIONS

This application claims priority from Australian Provisional Patent Application No. 2007903117 entitled "Improved Sensor System" filed 8 Jun. 2007, the entire contents of which are incorporated herein by reference.

FIELD OF THE INVENTION

This invention relates to an improved sensor system and also to methods of diagnosis using the system.

BACKGROUND OF THE INVENTION

Many devices have been used and proposed for recording body movements, and breathing movements. One example is ECG measurements which require the application of ECG electrodes to a patients skin are able to provide "one off" diagnostic information, as well as being used over a period of time for patient monitoring.

U.S. Pat. No. 5,989,193 (the entire contents of which are incorporated herein by reference) by the same inventor as the subject invention, discloses a device and method for detecting and recording the snoring of a patient. This device relies on pressure detectors or accelerometers, placed on or under the patient's mattress. The pressure detector is typically a piezoelectric transducer and the accelerometer may comprise an integrated circuit containing a floating piezoelectric transducer.

International Patent Application No PCT/AU01/00732 also by the same inventor, discloses a biophysical sensor which includes a PVDF (polyvinilidene fluoride) sound vibration sensing element and two or more signal processing paths for producing output signals. Output signals may be two or more of heart sounds, heart movement breathing movement and breath sounds.

However the problem with existing sensors is that they can be intrusive and have to be attached or pressed directly against a patient's chest wall or the like—as in the case of stethoscopes and ECG devices. In the case of those sensors built into e.g. mattresses which a patient lies on, these do not always reliably pick up sounds such as breath sounds. This is due in part to the number of layers of material that the sensor must detect sound through such as the patient's clothing, bed sheets, mattress cover etc. Also the sensors may make the mattress uncomfortable and disturb the patient's sleep.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

In a first aspect, the present invention provides a sensor system comprising:
a mat for placement over a patient's mattress;
at least one sensor and preferably a plurality of sensors, located in the mat;
the sensor or sensors including
a sensor housing, a sound vibration sensing element in the form of a piezoelectric membrane, and means for amplifying sensed sounds; and wherein the membrane is coated/covered with a flexible and/or deformable, typically impedance matching, layer which transfers high frequency breath sounds to the membrane without significant attenuating those high frequency breath sounds.

Advantageously the present invention provides a sensor which automatically provides for auscultation, in which the patient's own weight, from the patient lying on the bed, compresses their thorax against the membrane, compressing also the patient's clothing, bed sheet and mattress cover material between the two. The recoil in the mattress opposes the body mass, thus compressing the membrane against the thorax. The impedance matching layer on top of the membrane transmits the breath sounds through to the membrane.

Preferably, the membrane is a PVDF membrane.

The impedance matching layer is most preferably latex. The latex does not weaken or attenuate the fine breath sounds but transmits them to the PVDF membrane.

A patient will typically generate three specific categories of periodic movements/vibrations when lying down and breathing.

The first category periodic movement/vibration is generated by the muscular act of breathing. Breathing is generated by the repetitive contraction and then relaxation of the diaphragm and intercostal muscles that expand the chest wall and the lungs. The paired diaphragm muscles form a dome within the thoracic cavity. When the diaphragm muscles contract, they shorten and the dome descends, acting as a piston sucking air into the lungs, and displacing the abdominal contents along the long axis of the body, and generating a vacuum within the lungs that leads to air flow. When the subject is lying down, this breathing movement leads to a generally horizontal displacement. The signals generated by this cyclic horizontal displacement are relatively large in amplitude and are easily detected. These are low frequency movements and are generally relatively easily detected. These movements have a relatively high gain with a relatively low frequency of less than a few Hz. Similarly, the action of the pumping heart also generated a periodic movement.

The second category of vibrations is generated by air flowing in and out of the lungs during the act of breathing. The vibrations are the result of turbulent air flow that occurs along the airways (at the larynx, which is a mechanical constriction, and at the many points where the airways divide) that in turn generate very fine airway wall vibrations that are transmitted through the lung tissue to the chest wall. These normal air flow linked vibrations are called breath "sounds" as they are typically detected by the use of a stethoscope placed on the subject's chest wall. The stethoscope is a mechanical transducer amplifier that converts the very fine vibrations (that are not perceptible with to the naked ear or to manual palpation) into an audible signal so that a clinician can readily detect the presence or absence of air flow entering and exiting the lungs during breathing movements. These very fine vibrations have a relatively higher frequency (e.g. between 100 and 2000 Hz, with a "white noise" characteristic (i.e. a spread of frequencies) in which the typical frequency range is between 200 and 600 Hz. However, the relative gain is of very low amplitude.

The third category of periodic movement/vibrations is generated by abnormal activity within the body and includes pathological breathing, heart and gut "sounds". The abnormal lung sounds include wheezing, and crepitations. Wheezing is the result of airway vibration at points of airway narrowing, and crepitations are generated by the explosive opening of airways that wither and collapse during expiration or are blocked by mucus. These vibrations are often higher in amplitude that normal breath sounds, but have characteristic frequency time patterns. Another characteristic vibration in this category of movement/vibrations is snoring. Snoring is typically the audible sound generated by a vibrating upper airway (the airway outside the lungs, and typically at the soft palate/tongue region). Importantly, the frequency characteristics of snoring are different from those of the breath sound, and typically have spectral peaks of vibration ranging from as low as 20 Hz, up to several hundred Hz. In addition, the relative amplitude of snoring is greater that that of normal breath sounds.

The relative gain of breath sounds, to those of snoring, and then of breathing movements are 1 for breath sounds (the lowest amplitude of vibrations), 100 times for snoring, and 1000 to 10,000 times for breathing movements.

The major challenge for a system that can detect and faithfully record these three different categories of periodic movement/vibrations is to be capable to covering a wide frequency range, and a wide amplitude range.

In the current invention, these vibrations appear at the patient's chest wall and are transmitted to the PVDF membrane where the patient is lying on a sensor. Although the low frequency high amplitude periodic movements are relatively easy to detect, the low amplitude high frequency vibrations are easily attenuated and lost and "swamped" by the larger amplitude signals. However the current invention provides for an impedance matching layer, typically latex, that transmits the vibrations that appear at the chest wall without attenuating them significantly. Further, sensor preferably includes a floating silicone housing which optimises the way in which the different periodic movement/vibrations are detected by the piezoelectric membrane. The very large movement of breathing results in a horizontal deflection and subsequent distortion of the piezoelectric membrane generating a relatively large signal. In contrast, the fine vibrations generated by air flow arrive at the sensor surface in a vertical direction causing the membrane, which is the vibrating element of a drum, to vibrate. The silicone housing and the latex pad act as both a "collector" of the vibrations from the chest wall and an impedance matching element to enable that vibration energy to vibrate the active piezoelectric detecting membrane.

Being flexible and resiliently deformable, the latex is also comfortable to lie on, in contrast to say rigid layers of material which may not attenuate vibrations but could not be used for reasons of lack of patient comfort.

It is preferred that the mat comprises foam rubber and may typically be about 5 cm thick. The sensors may be mounted in holes formed in the foam rubber. Preferably biasing means are provided to bias the membrane/latex layer upwards in use against the patient. The mat is intended to the used in conjunction with a normal mattress as a mattress overlay. Thus, the underlying mattress acts to provide a support for a potentially wide range of body sizes, while the thin mat acts as a support and housing for the sensors. A particular advantage of housing the sensors in a mat is that the user does not have to position the individual sensors. The sensor array is such that the subject need only place the mat on a normal bed with the correct orientation), and the appropriate placement of the sensors is achieved as a result.

The sensor housing may be a thin flat cylinder and may be mounted in an elastomeric envelope/container (preferably made of silastic) for mounting the sensor in the mat. In a preferred embodiment, the envelope defines a continuous upper surface, defining a central portion beneath which a recess is defined having depending side walls forming a circle and an internal flange for mounting the sensor housing therein.

A circular external flange is provided for mounting the envelope over a circular aperture in the mat and a relatively thinner portion connects the flange to the central portion of the envelope. The central portion of the envelope may protrude relative to the external flange and act as a biasing means to bias the sensor into contact with the patient, in use.

Alternatively, other biasing means such as a spring mounted below the sensor could be used.

Preferably, the mat is rectangular and is sized to fit on top of a typical mattress. It has been found that having four sensors arranged in the second quarter of the mattress measured from the top edge/head arranged in a diamond formation ensures that at least one sensor is positioned against a patient's thorax to record breath sounds.

In a related aspect, the present invention provides a sensor for use in the system of the first aspect comprising a sensor housing, a sound vibration sensing element in the form of a membrane, and means for amplifying sensed sounds; and wherein the membrane is coated/covered with an impedance matching layer, most preferably latex.

The membrane should be large enough to record the fine vibrations of normal breathing generated air flow in and out of the lungs, but not so big as to be uncomfortable for the patient or create large holes in the mat. A membrane/housing diameter of 30 to 50 mm is preferred, most preferably about 40 mm.

In a related aspect the present invention provides a method of monitoring a patient comprising recording and listening to or analysing the low and high frequency breath sounds generated by the patient using the sensor system as described above.

More specifically there is provided a method of detecting sleep apnoea in a patient lying on top of the sensor system of the present invention comprising the steps of recording and listening to or analysing the low and high frequency breathing sounds generated by the patient and in particular listening to or analysing breathing characteristic of obstructive apnoea by using the high frequency breath sounds to detect when breathing efforts are made without resultant air flow.

In a related aspect there is provided a method of detecting asthma in a patient lying on top of the sensor system of the present invention comprising the steps of recording and listening to or analysing the low and high frequency breathing sounds generated by the patient and in particular listening to or analysing the high frequency sounds to detect wheezing.

In a yet further related aspect there is provided a method of detecting the onset of heart failure in a patient lying on top of the sensor system of the present invention comprising the steps of recording and listening to or analysing the low and high frequency breathing sounds generated by the patient and in particular listening to or analysing the high frequency sounds to detect crepitations.

BRIEF DESCRIPTION OF THE DRAWINGS

A specific embodiment of the present invention will now be described by way of example only and with reference to the accompanying drawings in which:

FIG. 2 shows a sensor system incorporating the sensor mat of FIG. 1; and

FIG. 3 is a schematic side view of a patient lying on the sensor mat of FIG. 2

DETAILED DESCRIPTION OF A PREFERRED EMBODIMENT

Figure 1:
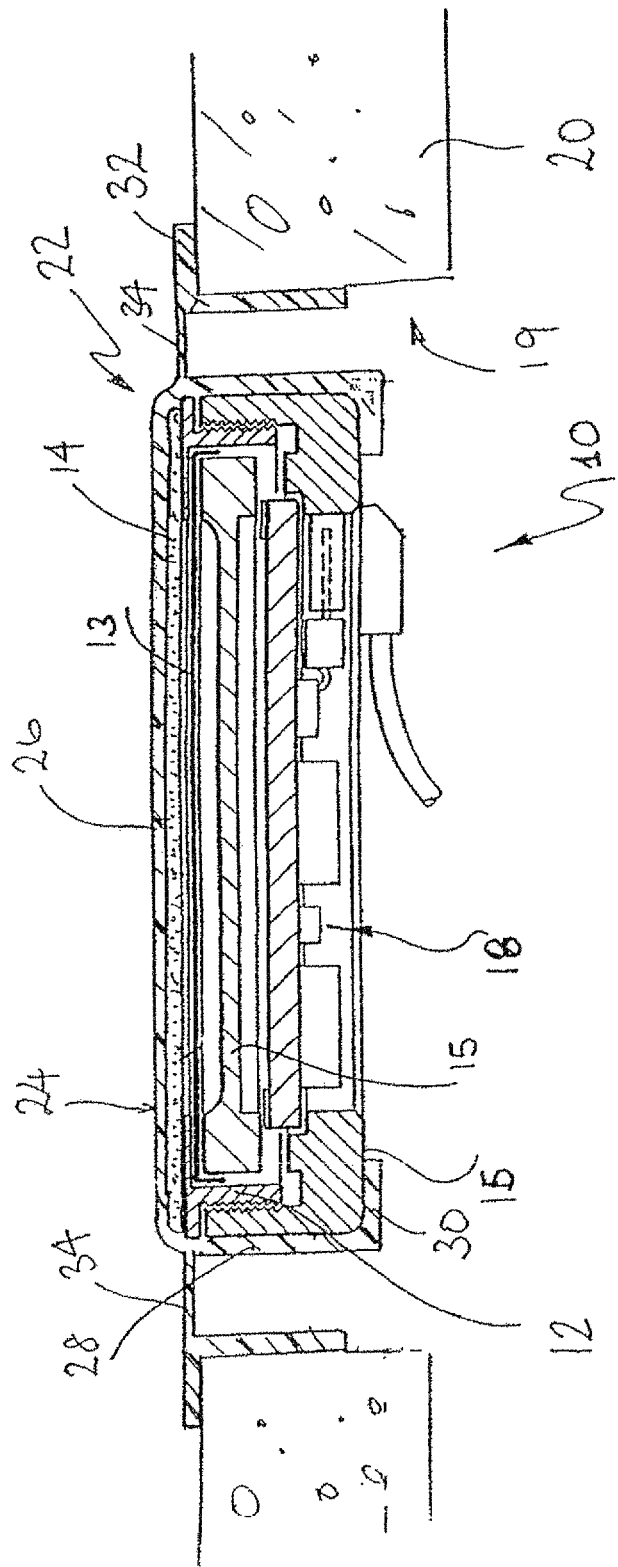
FIG. 1 is a cross sectional view through a sensor and mounting envelope mounted in a mat.

Referring to FIG. 1, an acoustic sensor 10 comprises a cylindrical aluminium body 12 having a sensor membrane in the form of a diaphragm of PVDF material 13 across its top. PVDF is a polymer with piezoelectric properties that it uses to generate electrical signals in response to acoustic and pressure vibration signals received. A thin 1-2 mm layer of an impedance matching material such as latex rubber 14 is located over the top of the sensor membrane 13.

The cylindrical body 12 extends at the top 15 to shield the diaphragm 13, and an aluminium ring 16 locks it in place and provides a live connector. Signals received at the sensor are analysed using built in circuitry mounted on a printed circuit board 18 to provide two or more electronic outputs. The outputs enable the recording and monitoring of signals of different frequency and, of particular significance, widely different amplitude, directly from a single sensor.

The complex signals generated from the patient may incorporate cardiac, respiratory and movement information, and they cause the membrane to vibrate. This vibration produces a weak potential difference across the membrane that is detected, amplified and filtered by the electronics.

The electronics have been mounted immediately adjacent to the membrane, within the sensor housing, using surface-mounted components. This obviates the need for the initial signal (which is in the range of 0 to 10 microvolts) to be conducted out of the sensor to processing electronics via a relatively long cable. Such cabling always causes degradation of the signal due to electromagnetic interference, movement of the cable and power loss due to cable resistance. Thus, no loss of signal is experienced in this way, as the connection is incorporated in the sensor housing.

The sensor has the ability to transduce a complex biological signal and provide two or more outputs. These outputs are in separate parts of the frequency spectrum of the biological signal and have different amplitudes within that signal. This processing within the sensor may be as described in International Patent Application No PCT/AU01/00732 discussed in the introduction, to this application the entire contents of which are incorporated herein by reference The sensor housing 12 is mounted in an elastomeric envelope/container 22 in a cylindrical hole 19 in a foam rubber mat 20 which is typically be about 5 mm thick.

The elastomeric envelope/container 22 for mounting the sensor in the mat is also circular in plan view and defines a continuous upper surface 24 defining a circular central portion 26 beneath which a recess is defined having depending side walls 28 forming a circle and an internal flange 30, for mounting the sensor housing therein.

A circular external flange 32 is provided for mounting the envelope above a circular aperture 19 in the mat 20 and a relatively thinner portion 34 connects the flange 32 to the central portion 26 of the envelope. The central portion 26 of the envelope protrudes relative to the external flange 32 and the envelope including the thinner portion 34 acts as a biasing means to bias the sensor into contact with the patient, in use.

With reference to FIGS. 2 and 3 the mat 20 is rectangular and is sized to fit on top of a typical mattress 50. It has been found that having four sensors 10 arranged in the second quarter of the mattress measured from the top edge, arranged in a diamond formation ensures that at least one sensor is positioned against a patient's thorax to record breath sounds as the patient twists and moves during sleep.

Alternatively, other biasing means such as a spring mounted below the sensor could be used.

The sensors are connected to an interface box 100 mounted in the mat at its head. The interface box contains the circuitry to process the signals to produce an output which passes to a recorder 110. Optional external sensors may provide signal inputs to the interface box such as room sound 112, event markers 114, oximeter readings 116, pressure 118, nasal flow 120.

In use the mat 20 containing the four sensors is placed on top of the patient's mattress and typically covered with a hospital grade mattress cover (known as "staph check") that can tolerate a wet bed and a sheet. The patient 200, typically wearing bed clothes lies on top of the mattress and mat. Breath sounds are very fine low amplitude vibrations that are transmitted from the lungs to the chest wall. These must be picked up by one or more of the sensors for the entire night's sleep of the patient.

Locating the four sensors in the diamond pattern in the second quarter of the mat ensures that at least one sensor is positioned to record breath sounds. The patient's own weight, from the patient lying on the bed, compresses their thorax against the PVDF membrane 13, compressing also the patient's clothing, bed sheet and mattress cover material housing 26 and latex layer 14 between the two. The recoil in the mattress opposes the body mass, thus compressing the membrane against the thorax and the thin membrane 34 biases the sensor against the patient's chest (through the sheet mattress protector ("staph-check") and patient's bed clothes. The impedance matching latex layer on top of the membrane transmits the breath sounds through to the membrane 13 where the vibrations generate charge. A high gain amplifier amplifies the signal.

The disposition of the sensors and the biasing means which is firm but not intrusive still allows the patient to lie in bed in comfort without irritation caused by the sensors. The mat is easy to use-placing the top edge at the top of the mattress ensures that the sensors are correctly located for recording sounds.

A patient will typically generate three specific categories of periodic movement/vibrations when lying down and breathing. These are:
1) the periodic movements of breathing;
2) the fine vibrations generated by air flowing in and out of the lungs during normal breathing (also known as breath "sounds"), and;
3) pathological vibrations (that include snoring, wheezing and crepitations).

The first category of low frequency periodic movement/vibrations are associated with movement of their chest wall and diaphragm during the act of breathing. The signals generated by such large movements are generally horizontal (as the patient is lying down) low frequency movements and are generally relatively easily detected. However, the second and third categories of vibrations are generated by air flowing into the lungs and by pathological vibrations such as wheezing, which are higher frequency and of a much lower amplitude are much harder to detect. These vibrations appear at the patient's chest wall and are transmitted to the PVDF membrane where the patient is lying on a sensor. Such high frequency sounds are easily attenuated and lost. The impedance matching layer, typically latex, transmits the sounds without attenuating them significantly. Being flexible and resiliently deformable, the latex is also comfortable to lie on, in contrast to say rigid layers of material which may not attenuate sounds but could not be used for reasons of lack of patient comfort.

A significant aspect of this sensor system is that it can detect the presence of normal air flow when the subject is breathing, and similarly can detect the absence of such airflow when the subject continues to make breathing efforts (the characteristic features of an obstructive apnoeic event).

The sensor system can be used to detect pathological vibrations during breathing. These include the vibrations generated by snoring, the vibrations that are generated by obstructed lung airways in asthma (which in turn are the origin of wheezing) and are characteristic of asthma, and the vibrations that generate crackles and crepitations (which are the result of fluid accumulation in the lung tissues and airspaces) and which are characteristic of heart failure.

The sensors will not only sense higher frequency breath vibrations but also low frequency breathing movement of the patient (i.e. the physical inhalation and exhalation of the lungs). In particular, the sensor may include software and circuitry for filtering and separating the two signals.

In a variant, not shown, a rigid fibreglass layer is sandwiched between two layers of latex on top of the membrane 13 to prevent the PVDF membrane which is brittle and friable, from accidental puncture. The layer is typically around 0.2 mm thick and its diameter is large enough that its edges touch the rim of the sensor housing, if compressed, thereby protecting the membrane The sensors may also be incorporated in a mattress rather than in a mat to lay on top of the mattress.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A sensor system comprising:
   a mat having an upper surface adapted to receive a patient, the mat comprising at least one hole, the hole having an upper opening at an upper surface of the mat and a bottom surface recessed from the upper surface of the mat;
   at least one acoustic sensor including:
      a sensor housing, and
      a sound vibration sensing element in the form of a membrane, the membrane being supported by the housing; and
      a flexible and/or deformable layer covering the membrane, the flexible and/or deformable layer being configured to transfer relatively high frequency breath sounds to the membrane without significantly attenuating those high frequency breath sounds, and
   the system further comprising:
   a mount that mounts the acoustic sensor in the hole, the mount being formed independently of the hole, the mount comprising:
      a flange engaging the upper surface of the mat at one or more positions around the upper opening of the hole; and
      a connection portion extending between the flange and the acoustic Sensor,
   wherein the mount suspends the acoustic sensor at a position spaced above the bottom surface of the hole and resiliently biases the acoustic sensor upwardly such that an upper surface of the sensor is located above the upper opening of the hole.

2. A sensor system as claimed in claim 1 wherein the membrane is a polyvinilidene fluoride (PVDF) membrane.

3. A sensor system as claimed in claim 1 wherein the flexible and/or deformable layer is latex.

4. A sensor system as claimed in claim 1 wherein the mat comprises foam rubber.

5. A sensor system as claimed in claim 4 wherein the foam rubber comprises a layer which is about 5 cm thick.

6. A sensor system as claimed in claim 1 wherein the upper surface of the acoustic sensor is biased upwards in use.

7. A sensor system as claimed in claim 1 wherein the sensor housing is a thin flat cylinder.

8. A sensor system as claimed in claim 1 wherein the mount defines a continuous upper surface having a central portion beneath which a recess is defined having depending side walls and an internal flange for mounting the sensor housing therein;
   wherein the connection portion connects the flange to the central portion, and wherein the connection portion is thinner than the central portion and/or the flange.

9. A sensor system as claimed in claim 8 wherein the central portion protrudes upwardly relative to the flange.

10. A sensor system as claimed in claim 1 wherein the mat is rectangular and is sized to fit on top of a mattress.

11. A sensor system as claimed in claim 10 wherein the sensor system includes four acoustic sensors arranged in the second quarter of the mattress measured from a top edge/head of the mattress, and arranged in a diamond formation such that, in use at least one acoustic sensor is configured to be positioned against the patient's thorax to record breath sounds.

12. The sensor system of claim 1, wherein the flexible and/or deformable layer is an impedance matching layer.

13. The sensor system as claimed in claim 1, wherein the mount comprises elastomeric material.

14. The sensor system as claimed in claim 1, wherein the acoustic sensor comprises an amplifier to amplify sensed sounds.

15. A sensor system comprising:
   a mat having an upper surface adapted to receive a patient, the mat comprising at least one hole, the hole having an upper opening at an upper surface of the mat and a bottom surface recessed from the upper surface of the mat;
   at least one acoustic sensor including:
      a sensor housing, and
      a sound vibration sensing element in the form of a membrane, the membrane being supported by the housing; and
   a mount that mounts the acoustic sensor in the hole, the mount comprising:
      a flange; and
      a connection portion;
      wherein the flange engages the upper surface of the mat at one or more positions around the upper opening of the hole, and wherein the connection portion is connected between the flange and the acoustic sensor such that the acoustic sensor is suspended in the hole and resiliently biased upwardly such that an upper surface of the sensor is located above the upper opening of the hole.

16. The sensor system as claimed in claim 15, wherein the mount is an elastomeric envelope/container.

17. A sensor system as claimed in claim 15 wherein the mount defines a continuous upper surface, having:

a central portion beneath which a recess is defined having depending side walls and an internal flange for mounting the sensor housing therein;
wherein the connection portion connects the flange to the central portion of the envelope, the connection portion being thinner than the central portion and/or the flange.

* * * * *